United States Patent [19]

Edl et al.

[11] Patent Number: 4,882,442

[45] Date of Patent: Nov. 21, 1989

[54] PROCESS FOR THE PRODUCTION OF EPOXIDES

[75] Inventors: Wolfgang Edl, Grosshesselohe; Günter R. Sienel, Ebenhausen, both of Fed. Rep. of Germany

[73] Assignee: Peroxid-Chemie GmbH, Munich, Fed. Rep. of Germany

[21] Appl. No.: 150,004

[22] Filed: Jan. 27, 1988

Related U.S. Application Data

[63] Continuation of Ser. No. 790,796, Oct. 24, 1985, abandoned, which is a continuation of Ser. No. 580,787, Feb. 22, 1984, abandoned, which is a continuation of Ser. No. 330,985, Dec. 15, 1981, abandoned.

[30] Foreign Application Priority Data

Dec. 30, 1980 [DE] Fed. Rep. of Germany ....... 3049434

[51] Int. Cl.$^4$ ............................................ C07D 301/12
[52] U.S. Cl. .................................................... 549/525
[58] Field of Search .......................................... 549/525

[56] References Cited

U.S. PATENT DOCUMENTS 2,838,524  6/1958  Wilson ................................ 549/525
2,875,178  2/1959  Greenspan et al. ................. 549/525
2,899,446  8/1959  Marks ................................. 549/525

FOREIGN PATENT DOCUMENTS 2835940  2/1980  Fed. Rep. of Germany .
1250047  11/1960  France .
 855199  11/1960  United Kingdom .
 877632  9/1961  United Kingdom .

OTHER PUBLICATIONS

Korach et al., Jour. Am. Chem. Soc., vol. 82 (1960) pp. 4328-4330.

Primary Examiner—Richard L. Raymond
Attorney, Agent, or Firm—Felfe & Lynch

[57] ABSTRACT

Process for the production of epoxides by reaction of one mol equivalent of the corresponding olefins with 1 to 2.6 mols equivalent aliphatic percarboxylic acids with 2-4 C atoms containing at least one strong acid, wherein the strong acid in the percarboxylic acid mixture is neutralized with an at least equivalent amount of an inorganic base and thereafter the percarboxylic acid mixture is combined with a reaction mixture containing the olefin, about 0.5 to about 0.74 equivalents acid-binding agent with reference to the amount of total carboxylic acid present in the percarboxylic acid mixture and, if necessary, solvent.

20 Claims, No Drawings

PROCESS FOR THE PRODUCTION OF EPOXIDES

This application is a continuation, of application Ser. No. 790,796, filed Oct. 24, 1985, now abandoned, which is a continuation of Ser. No. 580,787, filed Feb. 22, 1984, now abandoned; which is a continuation of Ser. No. 330,985, filed Dec. 15, 1981, now abandoned.

This invention relates to a process for the production of expoxides, particularly for the production of acid-labile epoxides.

Epoxides (oxiranes) are valuable intermediates, e.g. in the manufacture of odorants. Some terpene epoxides are also used as odorants.

The classical process for the preparation of epoxides is the so-called PRILESCHAJEW reaction, i.e. the epoxidation of olefins by means of percarboxylic acid (see D. Swern, Organic Peroxides, Volume II, Wiley-Interscience, 1981, 355–533).

Recently, the relatively stable, commercially available m-chloroperbenzoic acid, has frequently been used for epoxidation on a laboratory scale; however, for cost reasons it is unsuitable for use on an industrial scale. Of some technical interest are in particular the low molecular weight aliphatic equilibrium percarboxylic acids containing 2–4 C atoms, which are obtained by the reaction of the corresponding carboxylic acid with hydrogen peroxide (in as high a concentration as possible), in the presence of a small amount of a strong acid acting as catalyst, according to the following equation:

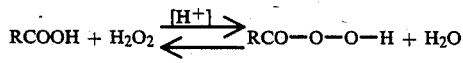

Equilibrium percarboxylic acids are thus a mixture of percarboxylic acid, carboxylic acid, hydrogen peroxide, water and strong acid. The composition depends on the molar ratio of carboxylic acid to $H_2O_2$ and the concentration of the hydrogen peroxide used. Sulfuric acid in a quantity of 0.5 to 1% is preferably used as the strong acid.

The preferred percarboxylic acid is peracetic acid, the commercial equilibrium peracetic acid (called PES-40) with the following approximate composition being used in particular:

| | |
|---|---|
| 40% peracetic acid | } total carboxylic acid |
| 40% acetic acid | |
| 5% hydrogen peroxide | |
| 14% water | |
| 1% $H_2SO_4$ | |

However, more dilute systems can also be used.

Perpropionic acid or perbutyric acids are particularly appropriate if treatment by distillation with respect to the boiling point is facilitated or made possible by their use.

All further details will be given on the basis of the system PES-40. However, the same basic principles apply to more dilute systems and analogous systems of other low molecular weight percarboxylic acids.

The preparation of a large number of epoxides with PES-40 in high yields and with a high degree of purity is unsuccessful because the epoxide initially formed reacts in a secondary reaction with acetic acid and/or water with ring opening, to give the corresponding hydroxy acetate or vicinal diol. These reactions are acid-catalysed so that the presence of sulfuric acid causes particular problems. Another undesirable secondary reaction is the acid-catalysed rearrangement of the epoxide to carbonyl compounds.

The eliminate the undesirable influence of sulfuric acid, it has therefore been suggested to neutralise with an inorganic base, e.g. sodium acetate, sodium hydrogencarbonate of calcium carbonate before adding the PES-40 to the olefin which, if necessary, is dissolved in a solvent (Swern, page 436). In the case of not excessively reactive epoxides, excellent results can be achieved with this so-called "buffered equilibrium percarboxylic acid".

This measure is insufficient for particularly acid-labile epoxides. In this case, the presence of the relatively large amount of acetic acid which is introduced together with PES-40 and is formed during the reaction, is obviously sufficient to effect ring opening. An addition, to the reaction mixture, of weak bases such as sodium carbonate and sodium hydrogencarbonate in an considerable excess to the amount necessary to neutralise all the mineral acid and the acetic acid permits an expoxidation to take place in such cases (Swern, p. 436). This method makes use of the fact that acetic acid (in methylene chloride) is neutralised approximately 2000 times more rapidly than peracetic acid (M. Korach et al, J. Am. Chem. Soc. 82, 4328 (1960)).

German patent application Ser. No. (DE-OS) 28 35 940 also suggests the above-mentioned, so-called "soda method" for the preparation of reactive, bicyclic terpene epoxides, e.g. α-pinene oxide, with PES-40. However, certain chlorinated hydrocarbons are necessary to achieve useful results. The practical implementation of the examples of DE-OS 28 35 940, however, gave greatly varying results as regards the yield and the purity of the product. It was found that there is a relationship between the conditions of agitation and the properties of the solid base with respect to both grain distribution and the surface structure so that the method is not reproducible.

It is therefore the objective of the present invention to overcome the disadvantages described above and to make a process available which permits epoxidation to be carried out in a high yield and with a high purity of the product under conditions reproducible at all times.

Surprisingly enough, it has been found that the difficulties described above can be overcome by neutralising the strong acid present in the percarboxylic acid before it is added to a reactive mixture of olefin, acid-binding agent and, if necessary, solvent if the amount of acid-binding agent, e.g. alkali carbonate or alkali hydrogen carbonate, is considerably reduced.

The subject matter of the invention is a process for the production of particularly acid-labile epoxides by the epoxidation of the corresponding olefins with aliphatic percarboxylic acids with 2–4 C atoms and containing strong acids in a solvent and/or excess olefin, characterized in that the strong acid is neutralised with an at least equivalent amount of an inorganic base before adding the percarboxylic acid to a reaction mixture, containing the olefin and about 0.5 to about 0.74 equivalents of acid-binding agent with reference to the amount of total carboxylic acid present in the percarboxylic acid mixture. An equivalent amount of inorganic base if preferred.

Acid-labile epoxides are those which undergo modification in the presence of low molecular weight carboxylic acids. In particular, they are derived from olefins which have two substituents or an aryl radical on at least 1 C atom of the olefinic double bond, or from cyclo-olefins, in particular from bicyclic terpenes. Examples of such olefins are: isobutene, 1,1,2-trimethyl ethylene, tetramethyl ethylene, styrene, acenapththylene, cyclohexene, 1-alkylcyclohexene alpha and beta-pinene, camphene, linalyl acetate, cedrene and calarene.

The preferred epoxidizing agents are solutions of the aliphatic percarboxylic acids with 2–4 C atoms, i.e. of perpropionic acid or perbutyric-acids and, in particular, of peracetic acid, in the corresponding carboxylic acid which, additionally, also contain a strong acid. Preferred solutions of this kind are the so-called equilibrium percarboxylic acids which are formed by the acid-catalysed reaction of carboxylic acid with hydrogen peroxide. Equilibrium peracetic acid, (PES-40) in particular, is preferred.

The term "equilibrium percarboxylic acid" is not intended to be restrictive to mean that a genuine equilibrium must be present. Rather, it is intended to indicate that, apart from percarboxylic acid, carboxylic acid and catalytic quantities of a strong acid are present—as well as water and hydrogen peroxide, if necessary. Consequently, genuine equilibrium systems subsequently modified, e.g. by the addition of an inert diluent, can be used according to the invention.

The strong acid present in the equilibrium percarboxylic acids usually consists of sulfuric acid in an amount of 0.5 to 1%. However, other strong mineral acids, such as phosphoric and nitric acid, and strong organic acids, e.g. alkane sulphonic acids, can be used.

The acid-binding agent used to neutralize the carboxylic acid preferably consists of alkali carbonates or alkali hydrogen carbonates, particularly sodium carbonate or sodium hydrogen carbonate. The quantity used depends on the sensitivity of the epoxide to the carboxylic acid used. Preferably, it is such that the carboxylic acid present is completely neutralized. However, approximately 75% of this amount is sufficient for less labile epoxides. In extreme cases, the carboxylic acid formed from the percarboxylic acid during the epoxidation reaction must also be combined. The acid-binding agent is added in the solid form.

The reaction is carried out in the presence of a solvent and/or excess olefin, in an amount sufficient to ensure that the reaction mixture can be stirred. Halogenated, and particularly chlorinated, hydrocarbons such as methylene chloride, chloroform, 1,2-dichloroethane, 1,2-dichloropropane, chlorobenzene and the preferred solvents (for kinetic reasons; Swern, page 459). However, other inert solvents such as benzene, toluene, ethyl acetate, dioxane can be used—though with correspondingly longer reaction times. Using the process according to the invention provides greater independence from the solvent than using the process according to DE-OS 28 35 940 according to which reasonably satisfactory results can only be achieved by using certain chlorinated hydrocarbons as the solvent.

The reaction temperature generally depends on the reactivity of the olefin; usually, it is between −20° and 60° C., preferably between 10° and 40° C. Higher temperatures should be avoided in order to keep decomposition of the percarboxylic acid as low as possible. For this purpose, well know peroxide stabilizers, such as 2,6-dipicolinic acid and hydroxyethane diphosphonic acid can also be added.

The inorganic bases for combining the strong acid can consist of the alkali or alkaline earth salts of the corresponding carboxylic acid, or the carbonates, hydrogen carbonates, oxides or hydroxides of the alkali or alkaline earth metals. They are preferably added in the solid form to the solution of the percarboxylic acid, however, aqueous, preferably concentrated aqueous, solutions can also be used. Precipitates which may form on addition of the inorganic base to the solution of percarboxylic acid can, if metering problems are likely to occur, be filtered off or dissolved by adding a small amount of water.

It is not of critical importance which of the inorganic bases is selected for use according to the invention: mild bases, such as carboxylates and carbonates, have the advantage that excess alkalization which would cause destabilization of the percarboxylic acid, is avoided even with excess concentrations. In the case of peracetic acid, sodium acetate, either in the anhydrous form or as the trihydrate, is particularly suitable. Another criterion of selection is that the content of heavy metal ions, which would also cause destabilization, should be as low as possible. It may therefore be appropriate to add suitable sequestering agents such as, in particular, heavy metal ion chelating agents, to the aqueous solution of the inorganic bases and/or the solution of the percarboxlic acid in order to combine undesirable heavy metal ions.

The following examples provide a more detailed explanation of the invention, without restricting it to these limits. In addition, the comparative examples 1 and 2 illustrate the surprising advance in the art of the process according to the invention compared with the process according to the state of the art.

All percentages given above and below represent percentages by weight.

EXAMPLES

For all the examples, commercial equilibrium peracetic acid (hereinafter abbreviated to PES-40) with the following composition was used:

| | |
|---|---|
| PES (peracetic acid) | 38.6% |
| Acetic acid | 44.5% |
| Hydrogen peroxide | 3.8% |
| Water | 12% |
| Sulfuric acid | 1% |

COMPARATIVE EXAMPLE 1 (ACCORDING TO DE-OS 28 35 940)

75.7 g (0.5 mole) 90% alpha-pinene, 187 g chloroform and 79.8 g (0.75 mole) anhydrous sodium carbonate are introduced into a 1 liter flask equipped with a stirrer, an internal thermometer, a reflux condenser and a dropping funnel.* Subsequently, 116.3 g (0.59 mole) PES-40 are added dropwise with cooling in the course of 1.5 hours in such a way that the reaction temperature is 40° C.

*and heated to 35° C.

Stirring is continued for 1 hour at 40° C., and subsequently 200 g water are added to the reaction mixture, whereby the sodium acetate formed is dissolved. The organic phase is separated off and washed again with 100 ml water.

After distilling off the chloroform under vacuum in the rotary evaporator, 89 g alpha-pinene oxide in a 61% concentration are obtained; this corresponds to a yield of 71% of the theoretical, based on alpha-pinene.

COMPARATIVE EXAMPLE 2 (WITH "BUFFERED EQUILIBRIUM PERACETIC ACID")

75.7 g (0.5 mole) 90% alpha-pinene are dissolved in 187 g chloroform and heated to 25° C. in the device described in comparative example 1. 116 g (0.59 mole) PES-40 to which 2 g (0.025 mole) sodium acetate had previously been added with stirring, are added dropwise* in the course of 1 hour in such a way that a reaction temperature of 30° C. is maintained. After an additional reaction time of 2 hours at 30° C., the sodium acetate formed is dissolved in 200 g water and the organic phase is analyzed by gas chromatography, with suppression of the solvent. The reaction mixture consists of 8.5% alpha-pinene oxide, 17.2% unreacted alpha-pinene and 74.3% byproducts.
*with cooling This example shows that alpha-pinene oxide is not stable under the reaction conditions indicated.

EXAMPLE 1

75.7 g (0.5 mole) 90% alpha-pinene, 187 g chloroform and 42.4 g (0.4 mole) anhydrous sodium carbonate are introduced into a 1 liter flask equipped with a stirrer, a reflux condenser, an internal thermometer and a dropping funnel and heated to 25° C. Subsequently, 116 g (0.59 mole) PES-40 to which 2 g (0.025 mole) sodium acetate have been added with stirring are added dropwise with brine cooling in the course of 1 hour in such a way that the reaction temperature is 30° C. Subsequently, agitation is continued for a further 2 hours at 30° C.

By adding 200 g water, the sodium acetate thus formed is dissolved, and after phase separation, washed with 100 g 7% sodium hydrogen carbonate solution.

After removing the chloroform in the rotary evaporator, 76 g alpha-pinene oxide with a 95% content are obtained; this corresponds to a yield of 95% of the theoretical, based on alpha-pinene.

EXAMPLE 2

In a 250 l stainless steel reactor equipped with, a reflux condenser, a metering device, a horseshoe mixer and a temperature indicator, 29.1 kg (211.4 mole) 99% alpha-pinene in 44.3 l chloroform/24.5 kg anhydrous sodium carbonate are caused to react by adding 51 kg (258.7 mole) PES-40 in which 853 g sodium acetate had previously been dissolved, at 28° to 30° C.

Following a 1.5 hour period of dropwise addition, agitation continues for a further 1.5 hours at 28° to 30° C.

Processing and isolation take place under the conditions indicated in example 1.

Result: 31.2 kg alpha-pinene oxide are obtained, corresponding to a yield of 94%. The gas chromatographic analysis gives a content of 97% with a chloroform content of 0.2% and an alpha-pinene content of <0.2%.

This example shows that the reaction according to the invention can be transferred without difficulty to a larger scale.

EXAMPLE 3

1032 g (5.0 mole) 99% alpha-cedrene, 2271 g chloroform and 532 g (5.0 mole) anhydrous sodium carbonate are introduced into a 10 l glass reactor equipped with a stirrer, reflux condenser, an internal thermometer and a dropping funnel and heated to 15° C.

Subsequently, 1183 g (6.0 mole) PES-40 to which 21 g (0.25 mole) sodium acetate had been added, are added dropwise in the course of 1 hour in such a way that the reaction temperature is 20° C. by applying brine cooling. Subsequently, agitation is continued for a further 3 hours at 20° C.

By adding 1750 g water, the sodium acetate thus formed is dissolved and, after phase separation, washed with 1000 g respectively of 7% sodium hydrogen carbonate solution and water.

After removing the chloroform in the rotary evaporator, 1114 g alpha-cedrene oxide with a content of 94% are obtained; this corresponds to a yield of 95% of the theoretical, based on alpha-cedrene.

EXAMPLE 4

In a 10 liter glass reactor, 991 g (5.0 mole) 99% linalyl acetate, 2180 g chloroform and 532 g (5.0 mole) anhydrous sodium carbonate are caused to react with 1183 g (6.0 mole) PES-40 to which 21 g (0.25 mole) sodium acetate had been added, by adding the PES-40 dropwise in the course of 1 hour at 20° C. This is followed by an additional reaction period of 2 hours at 20° C. and the sodium acetate formed is then dissolved by adding 1750 g water.

The organic phase is washed with 1000 g each of 7% sodium hydrogen carbonate solution and water, and the chloroform is subsequently distilled off in the rotary evaporator under a water jet vacuum at 50° C.

The yield of epoxylinalyl acetate is quantitative: 1072 g, with a content of 99%.

EXAMPLE 5

83 g (1.0 mole) 99% cyclohexene, 332 g dichloromethane and 106 g (1.0 mole) anhydrous sodium carbonate are introduced into a 2 liter round flask equipped with a stirrer, a reflux condenser, an internal thermometer and a dropping funnel, and heated to 25° C. 237 g (1.2 mole) PES-40 to which 4 g (0.05 mole) sodium acetate has been added, are added dropwise in the course of 1 hour with cooling in such a way that a reaction temperature of 30° C. is maintained. Stirring is then continued for a further 2 hours at 30° C. The sodium acetate thus formed is dissolved by adding 300 g water. After phase separation, the dichloromethane phase is washed once with 100 g 7% sodium hydrogen carbonate solution and subsequently subjected to fractional vacuum distillation using an efficiently separating column. The cyclohexene oxide obtained amounts to 93 g and has a content of 99%; this corresponds to a yield of 94% of the theoretical, based on cyclohexene.

EXAMPLE 6

104 g (1.0 mole) pure styrene, 260 g chloroform and 168 g (2.0 mole) sodium hydrogen carbonate are introduced into a 2 liter round flask equipped with a stirrer, a reflux condenser, an internal thermometer and a dropping funnel, heated to 35° C. and subsequently caused to react with a total ob 319 g (1.6 mole) PES-40 to which 8 g 0.1 mole) sodium acetate has been added, the PES-40 being added dropwise.

After a 9 hour reaction time, processing is carried out in the known way.

Result: 113 g styrene oxide with a 95% content; this corresponds to a yield of 89% of the theoretical, based on styrene.

EXAMPLE b 7

In a 1 liter double jacket reactor, 277.8 g (1.4 mole) PES-40 to which 8 g (0.1 mole) sodium acetate have been added, are added dropwise to 66.6 g (1.4 mole) condensed, pure isobutene, 324 g chloroform and 106 g (1.0 mole) anhydrous sodium carbonate at 5–10° C. A gas chromatogram produced after a 6 hour reaction time shows complete conversion of the isobutene to isobutene oxide.

Processing subsequently takes place in the known way—without distilling off the chloroform. This gas chromatogram—prepared while eliminating the solvent—shows an isobutene oxide content of 99%.

EXAMPLE 8

Batch:
138 g (1.0 mole) 99% alpha-pinene
303 g benzene
106 g (1.0 mole) anhydrous sodium carbonate
235 g (1.19 mole) PES-40 containing
4 g (0.05 mole) sodium acetate Method: execution and conditions corresponding to example 1, except for different reaction time, of 5 hours.

Result: 121 g alpha-pinene oxide with a content of 97%, corresponding to a yield of 77% of the theoretical, based on alpha-pinene. The low yield is attributable to an unsatisfactory separation of benzene and alpha-pinene oxide during processing by distillation in the rotary evaporator. The distillate (benzene) contained alpha-pinene oxide.

EXAMPLE 9

In a 10 l glass reactor, 2366 g (12.0 mole) PES-40 to which 41 g (0.5 mole) sodium acetate have been added, are added dropwise to 688 g (10.0 mole) cyclopentene, 2730 g dichloromethane and 1060 g (10.0 mole) anhydrous sodium carbonate during 1 hour in such a way that the reaction temperature is 30° C. by applying brine cooling. Subsequently, agitation is continued for further 3 hours at 30° C.

By adding 4000 ml water, the sodium acetate thus formed is dissolved and, after phase separation, washed with 1000 ml water. By rectification using an efficiently separating column, 876 g cyclopentene oxide with a content of 98% are obtained. The yield is quantitative.

EXAMPLE 10

In a 10 l glass reactor, 543 g (5.0 mole) cis, cis-cyclooctadiene-1.5, 4345 g chloroform and 1060 g (10.0 mole) anhydrous sodium carbonate are caused to react with 2563 g (13.0 mole) PES-40 to which 46 g (0.56 mole) sodium acetate had been added, by adding the PES-40 dropwise in the course of 2 hours at 20° C. This is followed by an additional reaction period of 3 hours. Then the sodium acetate formed is dissolved by adding 4000 ml water.

The organic phase is washed with 2000 g each of 7% sodium hydrogen carbonate solution and water, and the chloroform subsequently distilled off in the rotary evaporator under a water jet vacuum at 50° C.

690 g cis, cis-1.5-diepoxycyclooctane with a content of 95% are obtained; this corresponds to a yield of 94% of theory based on cis, cis-cyclooctadiene-1.5.

EXAMPLE 11

165 g (1.0 mole) cyclododecatriene-1.5.9, 500 g chloroform and 106 g (1.0 mole) anhydrous sodium carbonate are introduced into a 1 l glass reactor and cooled to 5° C. and subsequently reacted with 217 g (1.1 mole) PES-40 to which 4 g (0.048 mole) sodium had been added, by dropwise addition at the same temperature. After a 4 hour reaction time, processing is carried out in the known way. Solvent and unreacted triene are removed by fractional distillation.

Result: 158 g 1-epoxy-cyclododecadiene-5.9 with a content of 95%, corresponding to a yield of 84% based on cyclododecatriene-1.5.9.

What is claimed is:

1. A process for the production of an acid labile epoxide by reaction of one mole equivalent of the corresponding olefin with 1 to 1.6 moles equivalent of an aliphatic percarboxylic acid mixture of an aliphatic percarboxylic acid selected from the group consisting of peracetic acid, perpropionic acid, and perbutyric acid with a carboxylic acid corresponding to the percarboxylic acid and at least one strong acid; the process comprising: neutralizing said strong acid in the percarboxylic acid mixture with 1.0 to 1.785 equivalents of an inorganic base or a basic alkali or alkaline earth salt of said carboxylic acid, and thereafter combining the percarboxylic acid mixture with a reaction mixture containing said olefin in solvent in an amount sufficient to insure that the reaction mixture can be stirred, and about 0.5 to about 0.74 equivalents acid-binding agent with reference to the amount of total carboxylic acid present in said percarboxylic acid mixture while maintaining the temperature at −20° to 60° C.

2. The process of claim 1 wherein an equilibrium percarboxylic acid is used.

3. The process of claim 1 wherein an equilibrium peracetic acid is used.

4. The process of claim 1 wherein carbonates or alkali hydrogen carbonates are used as acid-binding agents.

5. The process of claim 1 wherein the alkali or alkaline earth salts of the carboxylic acid or the carbonates, hydrogen carbonates, oxides or hydroxides of the alkali or alkaline earth metals are used as the base to react with the strong acid.

6. The process of claim 6 wherein the percarboxylic acid is peracetic acid and the base is sodium acetate.

7. The process of claim 1 wherein the inorganic base is used in the form of a solid or a concentrated aqueous solution.

8. The process of claim 1 wherein a precipitate formed on addition of the inorganic base to the solution of percarboxylic acid is dissolved by adding water.

9. The process of claim 1 wherein a peroxide stabilizer is added to percarboxylic acid and/or the reaction mixture.

10. The process of claim 1 wherein a peroxide stabilizer is added to the reaction mixture from the series of chelating agents known to be peroxide stabilizers.

11. The process of claim 1 wherein the temperature is between 10° and 40° C.

12. The process of claim 1 wherein the mixture of percarboxylic acid with the reaction mixture containing the olefin and the acid-binding agent includes an inert solvent.

13. The process of claim 1 wherein the solvent is a chlorinated hydrocarbon.

14. The process of claim 1 wherein the olefin is present in excess and the solvent is present in an amount sufficient to ensure that the reaction mixture can be stirred.

15. A process for the production of an acid-labile epoxide comprising:

reacting 1 to 1.6 mole equivalents of an aliphatic percarboxylic acid mixture consisting of a percarboxylic acid, a carboxylic acid and a strong acid wherein said percarboxylic acid is selected from the group consisting of peracetic acid, perpropionic acid, and perbutyric acid, where said carboxylic acid corresponds to the percarboxylic acid and is acetic, propionic acid or butyric acid respectively, with 1.0 to 1.785 equivalents of an inorganic base of basic alkali or alkaline earth salt of the carboxylic acid to neutralize the strong acid; and thereafter combining the percarboxylic acid mixture with a mixture of one mole equivalent of an olefin corresponding to the epoxide and selected from the group consisting of isobutene, 1,1,2-trimethyl ethylene, tetramethyl ethylene, styrene, acenaphthylene, cyclohexene, 1-alkylcyclohexene, alpha-pinene, beta-pinene, camphene, linalyl acetate, cedrene and calarene, and about 0.5 to about 0.74 equivalents acid-binding agent referred to the amount of total carboxylic acid present in the reaction mixture.

16. The process of claim 15 wherein the strong acid is a mineral acid or an alkane sulphonic acid.

17. The process of claim 16 wherein the acid binding agent is sodium carbonate.

18. The process of claim 15 wherein the aliphatic percarboxylic acid mixture is peracetic acid mixed with acetic acid and sulphuric acid, and the acid binding agent is sodium carbonate.

19. The process of claim 15 wherein the aliphatic percarboxylic acid mixture is perpropionic acid mixed with propionic acid and sulphuric acid and the acid binding agent is sodium carbonate.

20. The process of claim 15 wherein the aliphatic percarboxylic acid mixture is perbutyric acid mixed with butyric acid and sulphuric acid, and the acid binding agent is sodium carbonate.

* * * * *

UNITED STATES PATENT AND TRADEMARK OFFICE
CERTIFICATE OF CORRECTION

PATENT NO. : 4,882,442
DATED : November 21, 1989
INVENTOR(S) : Wolfgang Edl, et. al.

It is certified that error appears in the above-indentified patent and that said Letters Patent is hereby corrected as shown below:

Column 2, line 68, "if" should read --is--.

Column 6, line 64, "ob" should read --of--.

Column 8, line 47, (new claim 6) "6" (second occurrence) should read -- 5--.

Signed and Sealed this

Sixth Day of July, 1993

Attest:

MICHAEL K. KIRK

Attesting Officer     Acting Commissioner of Patents and Trademarks